Feb. 8, 1955 C. MALLERIN Plant Pat. 1,349
ROSE PLANT
Filed April 29, 1954
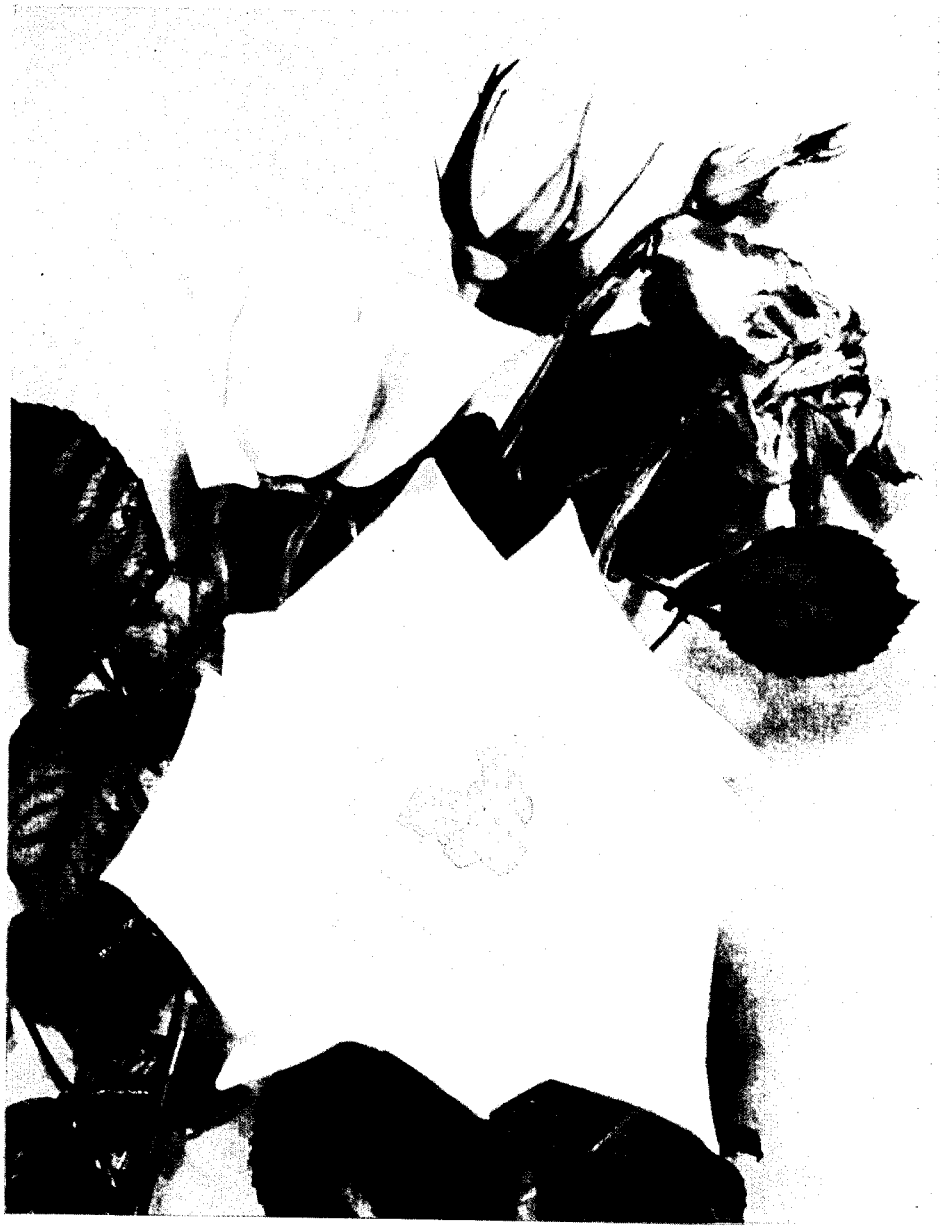
Inventor.
Charles Mallerin
By: Robb & Robb
Attorneys.

United States Patent Office

Plant Pat. 1,349
Patented Feb. 8, 1955

1,349

ROSE PLANT

Charles Mallerin, Par le Pont-de-Claix, France, assignor to The Conard-Pyle Company, West Grove, Pa., a corporation of Pennsylvania Application April 29, 1954, Serial No. 426,620

1 Claim. (Cl. 47—61)

The present invention relates to a new and distinct variety of rose plant of the hybrid tea class, originated by me as the result of crossing the variety "Soeur Therese" (unpatented) with the variety "Duquesa de Penaranda" (unpatented).

As the result of this breeding, my new variety is distinguished from its parents, as well as from all other varieties, by a unique and distinctive combination of characteristics, the dominating features of which are the unusual and remarkable range of color of its blooms, the very double form of its blooms, and its bright green, glossy foliage. In respect to the color of the blooms of my new variety, their general color effect varies from Empire Yellow to Empire Yellow suffused with an over-all pink coloration, the pink coloration usually appearing toward the latter part of the growing season, and becoming more pronounced as the blooms mature, which is a complete reversal of the usual tendency in other pink-tinged yellow rose varieties.

Repeated asexual reproduction of my new variety by budding, as performed in France, and also at West Grove, Pennsylvania, U. S. A., shows that the foregoing characteristics and distinctions come true to form and are established and transmitted through succeeding propagations.

The accompanying drawing shows typical specimens of the blooms and foliage of my new variety in different stages of development during the early part of the blooming season and as depicted in color as nearly true as it is reasonably possible to make the same in a color illustration of this character.

The following is a detailed description of my new variety, with color terminology in accordance with Ridgway's Color Standards and Nomenclature, except where general color terms of ordinary dictionary significance are obvious:

Type: Hardy; bush; outdoor; seedling; for cut flowers and for garden decoration.
Class: Hybrid tea.
Breeding: *Seedling.*
*Seed Parent.*—"Soeur Therese."
*Pollen Parent.*—"Duquesa de Penaranda."
Propagation: Holds its distinguishing characteristics through succeeding propagations by budding.

FLOWER

Locality where grown and observed: West Grove, Pennsylvania, U. S. A.
Flowers borne: Singly; on medium length stems of normal strength.
Quantity of bloom: Free, outdoors.
Continuity: Continuous.
Fragrance: Slight.
Bud:
*Peduncle.*—Medium length; medium caliper; erect; medium smoothness; with medium number of red hairs. *Color*—from Cosse Green, Plate V to Lettuce Green, Plate V.
*Before calyx breaks.*—Size—medium. Form—medium length; ovoid; with a conspicuous neck; with foliaceous appendages on the surface of the bud; with medium stout, much-cut, bristle-like foliaceous parts extending beyond the tip of the bud equal to ¾ or more of its length.
*As calyx breaks.*—Color—Light Yellow Green, Plate VI, shaded with Dull Green Yellow, Plate XVII; sometimes with reddish markings.

*As first petal opens.*—Size—medium. Form—medium length; ovoid. Color: outside—Strontian Yellow, Plate XVI; sometimes with slight markings of Begonia Rose, Plate I; inside—Lemon Chrome, Plate IV.
*Opening.*—Opens up well.
Bloom:
*Size (when fully open).*—Medium; from 3¼ inches to 4½ inches.
*Petalage.*—Very double; from 55 to 70 petals; arranged regularly.
*Form.*—Full at first, becoming hemispherical; outer petals being at first loosely rolled outward to long points; later, at maturity, having many of the petals of outer rows rolled outward to long points, with inner petals standing up in center; each petal tending to roll loosely outward along its outer edge.
Petals: Medium thickness; leathery; with both inside and outside satiny.
*Shape.*—Outer petals—narrowly obovate; generally with no notches, but occasionally with 1 or 2 notches. Intermediate petals—obovate; sometimes with no notches, but sometimes with 1 or 2 notches. Inner petals—obovate; irregular; with 1 or 2 notches.

This description of a newly opened flower was made from a rose grown outdoors in the month of July, at West Grove, Pennsylvania, U. S. A.:

*Color.*—Outer petal: outside surface—Evenly Citron Yellow, Plate XVI; inside surface—Pinard Yellow, Plate IV, shading to Lemon Yellow, Plate IV at base. Intermediate petal: outside surface—Barium Yellow, Plate XVI at outer edge, shading into an even Citron Yellow, Plate XVI; inside surface—Barium Yellow, Plate XVI at outer edge, shading to Lemon Yellow, Plate IV toward base, with Wax Yellow, Plate XVI at base. Inner petal: outside surface—Pinard Yellow, Plate IV, shading to Lemon Yellow, Plate IV at base; inside surface—Pale Lemon Yellow, Plate IV, shading to Lemon Chrome, Plate IV at base.

This description was made from a rose that was open for three days outdoors in the month of July, at West Grove, Pennsylvania, U. S. A.:

*Color.*—Outer petal: outside surface—Naphthalene Yellow, Plate XVI, shading to Straw Yellow, Plate XVI and to Citron Yellow, Plate XVI at base; inside surface—Barium Yellow, Plate XVI, shading to Pale Lemon Yellow, Plate IV, with point of attachment Lemon Chrome, Plate IV. Inner petal: outside surface—Barium Yellow, Plate XVI, shading to Lemon Chrome, Plate IV at point of attachment; inside surface—Amber Yellow, Plate XVI, shading to Lemon Chrome, Plate IV.
*General color effect.*—Newly opened flower—main body color Empire Yellow, Plate IV, with Barium Yellow, Plate XVI showing on inner surfaces of petals at outer edge. 3-days open—Empire Yellow, Plate IV mass effect at center, with Barium Yellow, Plate XVI at outer edge.

This description of a newly opened flower was made from a rose grown outdoors in the month of October, at West Grove, Pennsylvania, U. S. A.:

*Color.*—Outer petal: outside surface—Amber Yellow, Plate XVI, shading into Primuline Yellow, Plate XVI, and washed here and there with Light Jasper Red, Plate XIII; inside surface—Empire Yellow, Plate IV, shading into Light Cadmium, Plate IV, with a suffused Light Coral Red, Plate XIII at the outer edge. Intermediate petal: outside surface—Apricot Yellow, Plate IV, shading into Empire Yellow, Plate IV, and to Lemon Chrome, Plate IV at base; inside surface—Evenly Light Cadmium, Plate IV, but sometimes washed with Light Coral Red, Plate XIII in areas toward the outer edge. Inner petal: outside surface—Buff Yellow, Plate IV, shading into Apricot Yellow, Plate IV, and then to Empire Yellow, Plate IV; inside surface—Apricot Yellow, Plate IV, shading into Light Cadmium, Plate IV.

This description was made from a rose that was open for three days outdoors in the month of October, at West Grove, Pennsylvania, U. S. A.:

*Color.*—Outer petal: outside surface—Pinard Yellow, Plate IV at outer edge, shading to Empire Yellow, Plate IV at base; inner surface—Amber Yellow, Plate XVI, shading to Lemon Chrome, Plate IV at base; towards the outer edge, there is a suffused pink color which is not distinct enough to compare with a color chart, but which nevertheless gives a color effect to the flower when observed from a distance. Inner petal: outside surface—Baryta Yellow, Plate IV, shading into Pinard Yellow, Plate IV, and then to Empire Yellow, Plate IV at base; inner surface—a slightly lighter shade of color than Capucine Orange, Plate III at outer ⅓ of petal, becoming Empire Yellow, Plate IV, and then Lemon Chrome, Plate IV at base.

*General color effect (mature bloom).*—Empire Yellow, Plate IV, suffused with pink.

*Behavior.*—Persist for a time.

*Flower longevity.*—On bush in garden—4 days in August. Cut roses grown outdoors and kept at living-room temperatures—4 days in August.

REPRODUCTIVE ORGANS

Stamens: Many; arranged regularly about pistils.
Filaments: A few without anthers. Color—Lemon Chrome, Plate IV.
Anthers: All open at once; medium size; occasionally an anther fused with a petaloid. Color—Citron Yellow, Plate XVI.
Pollen: Abundant. Color—Lemon Chrome, Plate IV.
Pistils: Many.
Styles: Uneven; medium length; medium caliper; columnar.
Stigma: Color—Whitish Yellow.
Ovaries: Some protruding from calyx.
Hips: Ovoid: with inconspicuous neck; smooth; walls thick and fleshy. Color—russet.
Sepals: Permanent; moderately long; spear-shaped.
Seeds: Medium number; medium size.

PLANT

Foliage:

*Leaves.*—Compound of 5, but sometimes only 3 leaflets; normal abundance; medium size; leathery; glossy.

*Leaflets.*—Shape—oval, with apex acute, but sometimes mucronate. Base—obtuse. Margin—simply serrate.

*Color.*—Mature: upper surface—Forest Green, Plate XVII; under surface—Asphodel Green, Plate XLI. Young: Upper surface—Light Bice Green, Plate XVII; under surface—Lumiere Green, Plate XVII.

*Rachis (the supporting stem of the compound leaf).*—Medium caliper. Upper side—grooved; hairy; under side—sparsely prickly and thorny.

*Stipules.*—Medium length; moderately narrow; with short points turning out at an angle of more than 90°.

*Disease Resistance.*—Normal resistance to mildew and blackspot, as determined by comparison with other varieties grown under comparable cultural conditions at West Grove, Pennsylvania, U. S. A.

Growth:

*Habit.*—Bushy; much-branched.

*Growth.*—Free.

*Canes.*—Medium caliper.

*Main Stems.* — Color — Calla Green, Plate V. Thorns—several; medium length; hooked downward; with medium length, oval base. Prickles—none. Hairs—none.

*Branches.* — Color — Parrot Green, Plate VI. Thorns—several; medium length; hooked downward; with medium length, oval base. Prickles—several. Color—bronze. Hairs—none.

*New Shoots.*—Color—Biscay Green, Plate XVII. Thorns—several; medium length; hooked downward; with medium length, narrow base. Prickles—none. Hairs—none.

I claim:

A new and distinct variety of rose plant of the Hybrid Tea class, substantially as herein shown and described, characterized particularly as to novelty by the distinctive combination of the unusual color range of its blooms varying in general color tonality from Empire Yellow during the early part of the growing season to Empire Yellow suffused with an over-all pink coloration during the latter part of the growing season, which pink coloration tends to become more pronounced as the blooms mature, by the very double form of its blooms, and by its brought green, glossy foliage.

No references cited.